United States Patent
Zakharov et al.

(10) Patent No.: US 11,058,294 B2
(45) Date of Patent: Jul. 13, 2021

(54) DEVICE AND METHOD FOR MEASURING VIEWING DISTANCES

(71) Applicant: VIVIOR AG, Zurich (CH)

(72) Inventors: Pavel Zakharov, Volketswil (CH); Michael Mrochen, Eglisau (CH)

(73) Assignee: Vivior AG, Zurich (CH)

(*) Notice: Subject to any disclaimer, the term of this patent is extended or adjusted under 35 U.S.C. 154(b) by 143 days.

(21) Appl. No.: 16/090,776

(22) PCT Filed: Apr. 10, 2017

(86) PCT No.: PCT/EP2017/058494
§ 371 (c)(1),
(2) Date: Oct. 2, 2018

(87) PCT Pub. No.: WO2017/174817
PCT Pub. Date: Oct. 12, 2017

(65) Prior Publication Data
US 2019/0142268 A1    May 16, 2019

(30) Foreign Application Priority Data
Apr. 8, 2016 (EP) .................. 16164472

(51) Int. Cl.
*A61B 3/02* (2006.01)
*A61B 3/028* (2006.01)
(Continued)

(52) U.S. Cl.
CPC .............. *A61B 3/028* (2013.01); *A61B 3/09* (2013.01); *A61B 3/103* (2013.01); *A61B 5/0002* (2013.01);
(Continued)

(58) Field of Classification Search
CPC ... A61B 5/6803; A61B 5/6802; A61B 5/1072; G02C 11/10
(Continued)

(56) References Cited

U.S. PATENT DOCUMENTS

| 2,726,380 A | 12/1955 | Campisi |
| 3,379,885 A | 4/1968 | Nork |

(Continued)

FOREIGN PATENT DOCUMENTS

| CN | 103398695 | 1/2015 |
| CN | 105282472 | 1/2016 |

(Continued)

OTHER PUBLICATIONS

L. T. Thompson, J. R. Moyer, E. Akase, and J. F. Disterhoft, "A system for quantitative analysis of associative learning. Part 1. Hardware interfaces with cross-species applications.," J. Neurosci. Methods, vol. 54, No. 1, pp. 109-117, 1994.

(Continued)

*Primary Examiner* — Hung X Dang
(74) *Attorney, Agent, or Firm* — Williams Mullen; Thomas F. Bergert

(57) ABSTRACT

The present invention relates to a distance measuring system. The distance measuring system comprises a distance measuring sensor, a memory unit and a processing unit. The distance measuring sensor is adapted and arranged to measure viewing distances between a subject's eyes and one or more objects. The memory unit is adapted to store the measured viewing distances in a set of measured viewing distances. The processing unit is adapted to determine a statistical distribution of the measured viewing distances from the set of measured distances.

17 Claims, 14 Drawing Sheets

Figure 1:
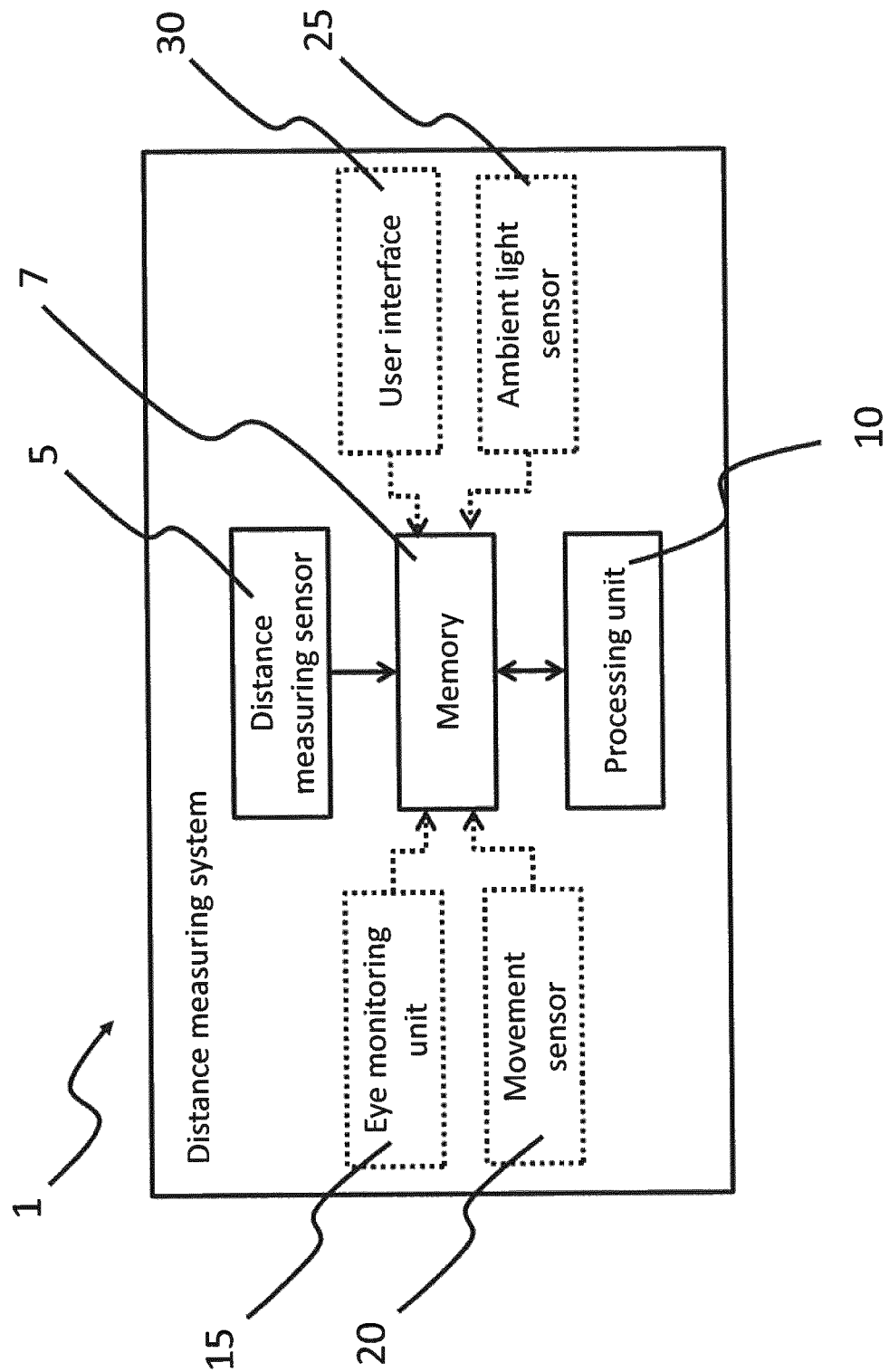

(51) Int. Cl.
   *A61B 3/09*    (2006.01)
   *A61B 3/103*   (2006.01)
   *A61B 5/00*    (2006.01)
   *A61B 5/06*    (2006.01)
   *A61B 5/107*   (2006.01)
   *A61B 5/11*    (2006.01)
   *A61B 5/16*    (2006.01)

(52) U.S. Cl.
   CPC .............. *A61B 5/06* (2013.01); *A61B 5/1072* (2013.01); *A61B 5/1114* (2013.01); *A61B 5/168* (2013.01); *A61B 5/6803* (2013.01)

(58) Field of Classification Search
   USPC ................................ 351/158, 237, 239, 246
   See application file for complete search history.

(56) References Cited

U.S. PATENT DOCUMENTS

| | | | |
|---|---|---|---|
| 3,863,243 | A | 1/1975 | Skolnick et al. |
| 4,953,111 | A | 8/1990 | Yamamoto et al. |
| 5,025,791 | A | 6/1991 | Niwa |
| 2003/0218721 | A1 | 11/2003 | Stern et al. |
| 2010/0194578 | A1 | 8/2010 | Zhang |
| 2011/0249237 | A1 | 10/2011 | Chernyak |
| 2012/0218253 | A1 | 8/2012 | Clavin |
| 2015/0196256 | A1 | 7/2015 | Venkatraman et al. |
| 2015/0288812 | A1 | 10/2015 | Ting |
| 2016/0300109 | A1* | 10/2016 | Aonuma ............... G06T 19/006 |

FOREIGN PATENT DOCUMENTS

| | | |
|---|---|---|
| JP | 3069568 U | 6/2000 |
| JP | 2013226397 | 11/2013 |
| JP | 2015058246 | 3/2015 |
| JP | 2015228992 | 12/2015 |
| KR | 1020160033376 | 3/2016 |
| WO | 2014126307 | 8/2014 |
| WO | 2014179857 | 11/2014 |

OTHER PUBLICATIONS

M. W. Johns, A. Tucker, R. Chapman, K. Crowley, and N. Michael, "Monitoring eye and eyelid movements by infrared reflectance oculography to measure drowsiness in drivers," Somnologie, vol. 11, No. 4, pp. 234-242, 2007.

A. Tucker and M. W. Johns, "The Duration of Eyelid Movements During Blinks: Changes with Drowsiness," Sleep, vol. 28, p. (Suppl) A122, 2005.

M. Johns, "The amplitude-velocity ratio of blinks: a new method for monitoring drowsiness," Sleep, 2003.

L. T. Young and D. Sheena, "Survey of eye movement recording methods", Behavior Research Methods & Instrumentation, vol. 7(5), 1975, pp. 397-429.

T. Leung et al, "A novel instrument for logging nearwork distance", Ophtalmic & Physiological Optics, 31, 2011, pp. 137-144.

European Patent Office, International Search Report and Written Opinion, PCT/EP2017/058494, dated Jul. 11, 2017.

Examination Report, Russian Patent Application No. 2018136418, Russian Federal Institute of Industrial Property, dated Jun. 19, 2020.

Japanese Patent Office, Office Action, JP Application No. 2019-503778, dated Dec. 8, 2020.

China National Intellectual Property Administration, Office Action, CN Application No. 201780021808.X, dated Dec. 3, 2020.

\* cited by examiner

DEVICE AND METHOD FOR MEASURING VIEWING DISTANCES

The present invention is directed to a distance measuring system and a method for measuring viewing distances between a subject, e.g. a user, and one or more objects in the subject's viewing direction. The device and method allow a determination of a statistical distribution of the measured viewing distances.

In ophthalmology, it is important to characterise and understand patient's vision requirements in order to customise a therapy to achieve best clinical outcome and a patient's satisfaction.

This is, for example, the case in the cataract surgery, when a natural crystalline lens is replaced by an artificial intraocular lens (IOL). Due to the limitations of the current technology, IOL lacks the ability to accommodate to different distances. Thus, the implanted monofocal artificial lens is set to a specific viewing distance defined by a refractive target. As a result the eye of the patient is fixed to a specific viewing distance and the patient has to use refraction correction means (such as glasses) to see sharp in other distances. Alternatively, a surgeon might suggest a premium refractive solution that can be a multifocal and aspheric IOL or a cataract surgery in combination with a corneal refractive surgery, which allows the patient to retain acceptable visual performance at a set of viewing distances. The refractive solution and refractive targets which are derived from the patient's viewing distance needs are chosen before surgery during an interview with the surgeon based on the patient's preferences. The patient consults the surgeon and explains his or her requirements based on personal habits, occupation, lifestyle and preferences. Thus, the decision is based on the patient's subjective perception of his or her habits and requirements, which may reflect misperceived vision needs. The consecutive choice of a refractive correction for an artificial lens may neglect required everyday accommodation needs.

For the laser refractive correction surgery, when presbyopia of the patient is taken into account (for example in presbyopia treatment), surgery has to be adjusted for the optimisation of visual performance for the specific viewing distances. Viewing distances outside of the optimised range would be compromised. Thus, during the surgery planning, a medical professional has to be able to understand the patient's visual requirements in order to better adjust the range of optimised vision performance for a specific patient. Any ophthalmic treatment or procedure which has to take into account limited accommodating performance of the eye irrespectively if it is induced by this procedure or by other factors would benefit from objective characterisation of the patient's visual habits and requirements.

Since the patient is subject to his own subjective perception, there is a need for a technique supporting a more objective decision for the selection of an artificial lens.

According to a first aspect of the present invention, a viewing distance measuring system comprises a distance measuring sensor, a memory unit and a processing unit. The distance measuring sensor is adapted and arranged to measure viewing distances between eyes of a subject, e.g. eyes of a user, and one or more objects. The viewing distances may be measured between the eyes of the subject and the one or more objects in the distance measuring sensor's viewing direction. The memory unit is adapted to store the measured viewing distances in a set of measured viewing distances. The processing unit is adapted to determine a statistical distribution of the measured viewing distances from the set of measured viewing distances.

The memory unit may be a storage unit, arranged in the distance measuring system, for example in a distance measuring device of the distance measuring system, on a connected mobile device, mobile or desktop personal computer. The memory unit may also be or be part of a cloud storage. That is, the memory unit may be part of the same device as the distance measuring sensor, e.g. part of the distance measuring device, or may be part of a different device than the distance measuring sensor. Similarly, the processing unit may be part of the same device as the distance measuring sensor and/or the memory unit, e.g. may be part of the distance measuring device, or may be part of a different device than the distance measuring sensor and/or the memory unit.

Activities and context recognition can be performed based on the statistical distribution derived from a history of measurements of a particular subject or multiple subjects. For example, an activity can have a similar signature in signals of various subjects and thus an algorithm can be trained to recognise the activity automatically.

The distance measuring sensor's viewing direction can be understood as the sensitivity of the distance measuring sensor or the subject's common or normal viewing direction. In such common or normal viewing direction, the subject's head can be turned into a direction of the one or more objects and the distance measuring sensor's viewing direction may be oriented into the subject's viewing direction. The subject may be understood as the person wearing a device including the distance measuring sensor, e.g. wearing the distance measuring device, e.g. a patient. The user may be understood as the person evaluating the statistical distribution, e.g. a medical professional such as a doctor.

The distance measuring sensor can be an optical, acoustical or an electromagnetic sensor, for example a LASER, SONAR, LIDAR or RADAR. The distance measuring sensor can be a time-of-flight optical sensor. Further, the distance measuring sensor can be an imaging sensor. The distance measuring system may contain two or more distance measuring sensors being able to obtain distances of multiple objects at the same time. For example, the two distance measuring sensors can be located on the left and right side of the subject's head, glasses or spectacles' frame. The distance measuring sensor can also be an imaging sensor, for example a camera, capable to acquire or derive three-dimensional scenes, for example a stereo image sensor in a double camera system, time-of-flight sensor or imaging sensor with a structured illumination.

The statistical distribution may indicate average and/or overall viewing distances viewed by the subject, e.g. a patient, over a certain period of time. The certain period of time may be one or more hours or one or more days. The statistical distribution can be in a form of histogram where viewing distances can be weighted. For example, the viewing distances can be weighted based on the frequency of their occurrence. The statistical distribution can be in a form of a histogram where viewing distances can be weighted based on the subject's feedback. Important periods may be elevated. Unimportant periods may be reduced. The subject can highlight or elevate a significant or an important time period or reduce an insignificant or unimportant time period.

The statistical distribution can be stratified based on the subject's activities and context and presented separately for each activity and context. Context-aware statistics might also include time spent in specific activities and context. If the data is used for a cataract surgery planning, the statistical distribution allows a medical professional to more objectively choose the right refractive power of an artificial lens to be implanted into the patient's eye. The context-aware statistics can allow the medical professional to choose a refractive solution based on the importance of a specific context to the patient.

In other words, the statistical distribution forms a more objective basis of decision-making for the medical professional.

The distance measuring system may further comprise an eye monitoring unit. The eye monitoring unit is adapted and arranged to detect the subject's eye direction relative to the distance measuring sensor's viewing direction. The processing unit may be further adapted to statistically weight, select or discard the measured viewing distances from the set of measured viewing distances based on the subject's eye direction relative to the distance measuring sensor's viewing direction. Eye monitoring measurements can be stored for further retrospective analysis. Discarded measured viewing distances may be neglected for determining the statistical distribution and thus not considered for determining the statistical distribution of the measured viewing distances. Selected measured viewing distances can be the most valuable viewing distances for a specific acquisition time or the only measured viewing distances to be measured during a subject's favourite activity. These selected measured viewing distances may be the only measured viewing distances considered for storing in the set of measured viewing distances and the only measured viewing distances considered for the statistical distribution. In one specific example, the subject's eye direction may be considered to be substantially different to the distance measuring sensor's viewing direction if the subject's eye direction is not parallel to the distance measuring sensor's viewing direction. The subject's eye direction may be defined as the direction of one of the subject's eyes, but may be defined as the direction of both of the subject's eyes.

Statistically weighting, selecting or discarding the measured viewing distances when the subject's eye direction is substantially different to the distance measuring sensor's viewing direction has the advantage to better indicate where the subject's (here a patient's) viewing distances are the most likely to occur. For example, viewing distances that only occur for a number of times that is below a predetermined threshold are not or at least less considered for determining the statistical distribution.

The distance measuring sensor can be a sensor array or an imaging sensor adapted to acquire distances of multiple objects at the same time. The processing unit can statistically weight, select or discard the measured viewing distances from the set of measured viewing distances simultaneously acquired from multiple objects based on the subject's eye direction relative to the distance measuring sensor's viewing direction.

In one or more embodiments, the eye monitoring unit may comprise any eye tracking functionality. Eye tracking is normally understood as the process of measuring either the point of gaze (where one is looking) or the motion of an eye relative to the head. An eye tracker is thus normally a device for measuring eye positions and eye movement.

The eye monitoring unit can further be adapted and arranged to detect the subject's eye blinks, the subject's eye motion, the subject's eye pupil size and/or crystalline lens accommodation. The subject's eye blinks, eye motion, pupil size and variations indicate whether the subject is paying attention to the viewed object or not. The subject's pupil variations under stable lightning conditions and the subject's eye direction can serve as an indirect sign of accommodative efforts and indicates importance of the object or scene for the subject. Pupil size, while viewing an object or scene, can also be taken into account as a weighting factor for visual requirements. Constricted pupils increase the depth of field and thus increase the visual tolerance of a refractive error, which can be accounted in the data analysis of the statistical distribution.

Direct measure of lens accommodation effort in the stable viewing direction serves as an indication of importance of the viewed object scene and thus also can be taken into account.

Further, the eye monitoring unit can be adapted and arranged to detect light reflections from an optical surface of the subject's eye. This light can be from an external (ambient) source or from a light source mounted on the device carrying the eye monitoring unit, e.g. the distance measuring device. The reflection from a corneal front surface as well as from a lens' surface allows for more precisely determining eye movements. At the same time, reflections from the lens' surface can be used for the measurements of the lens' accommodative changes. The eye monitoring unit can also determine the blinking and open and/or closure timing for the processing unit to derive the subject's mental state, wakefulness and drowsiness.

One or more, e.g. all, of the above-mentioned factors can be taken into account for determining the statistical distribution. In this respect, the processing unit can further be adapted to weight or to discard the measured viewing distances based on the subject's eye blinks, the subject's eye motion, the subject's pupil size and/or variation. For example, the processing unit can be adapted to weight, with a weighting factor smaller than one, or to discard the measured viewing distances that have been measured while/when the number of blinks of the subject's eye is higher than a predetermined threshold or for example when the subject is sleeping. Alternatively or additionally, the processing unit can be adapted to weight, with a weighting factor smaller than one, or to discard the measured viewing distances that have been measured while/when the motion of the subject's eye is higher than a predetermined threshold. Additionally, the subject's pupil variations under stable light conditions as indication of accommodative effort can be taken into account in the statistics. In this way, the attention the subject pays to the specific object/scene can be taken into account for determining the statistical distribution.

In one case, measurements of viewing distance can be discarded when subject's eyes are closed, for example during a blink, or during sleep.

Weighting the measured viewing distances comprises prioritizing or deprioritizing measured viewing distances by weighting the measured viewing distances with values smaller than one, e.g. equal to or close to zero, for deprioritizing and values higher than one for prioritizing.

The distance measuring system can further comprise a movement sensor. The movement sensor may be for example an accelerometer, a gyroscope, a magnetometer, an altimeter, a pedometer and/or a geopositioning device, or a combination thereof. The movement sensor can be adapted and arranged to measure movements of the subject's body, for example the subject's head. The processing unit can further be adapted to statistically weight, select or discard the measured viewing distances from the set of measured viewing distances based on the measured movements.

The distance measuring system can further comprise an ambient light sensor. The ambient light sensor can be adapted and arranged to measure ambient light, light intensity and/or spectral content in the distance measuring sensor's viewing direction. The processing unit can further be adapted to statistically weight, select or discard the measured viewing distances from the set of measured viewing distances based on the measured ambient light, light intensity and/or spectral content.

The ambient light sensor can further measure total integrated light intensity, specific spectral components and/or hue.

The distance measuring system can further comprise a proximity sensor. The proximity sensor can be used to detect if the device including the distance measuring sensor, e.g. the distance measuring device, is worn on the body and can control this device accordingly, for example, start measurement automatically, when this device is placed on or at the body.

The distance measuring system can further comprise a temperature and/or a humidity sensor. The temperature and/or humidity sensor can be used to identify an environment the subject is exposed to on a daily basis, the attention of the subject and the activities he or she is doing regularly. The environment can also be referred to as context or context information.

The distance measuring system can further comprise a user interface. The user interface can be adapted to receive a user input. The processing unit can further be adapted to weight, select or discard the measured viewing distances from the set of measured viewing distances based on the user input. The user interface can be for example a touch display, a button, a trigger, a proximity sensor, microphone and/or a tap detector. The user input can further be a head shake, an eye blink, an eye squint, eye movement, a hand gesture and/or voice command, wherein the user interface may comprise or be replaced by or be configured as the movement sensor or the eye monitor unit.

The user interface may be further adapted to generate a feedback signal for the subject. This feedback signal may be based on the measured distance and may be in the form of an acoustic, visual or haptic indicator. For example, the user interface may generate an alarm for the subject by a vibration of the distance measuring system or a connected cell phone when the subject is reading a book too close under inadequate lightning conditions.

The user input provides the advantage of getting feedback from the patient and assessing an activity he or she deems important or unimportant throughout the day.

Further, the distance measuring system can comprise a intermittent (triggered) measurement mode to be used by the subject. The user input can be used to initiate measuring viewing distances by the distance measuring system if the intermittent (triggered) measurement mode is used. For example, the distance measuring system might only perform measurements when the measurements are initiated by the subject (spot-measurements).

The distance measuring system can further be adapted to be mounted on glasses, spectacles' frame, a frame to be worn on or at the subject's head and/or adapted to be attached to the subject's head. The distance measuring system can be integrated in or arranged at or on glasses, the frame to be worn on or at the subject's head and/or a spectacles' frame respectively. Further, the distance measuring system could be attached to the subject's head by straps, to a helmet, to a headset, to hearing aid or headphones. The distance measuring system may be configured as or attached to a wearable device. Further the frame may be attachable to glasses. Further the frame may be foldable or bendable to fit in a storage case, for example a capsule.

The processing unit can further be adapted to calculate one or more refraction requirements from the viewing distances. The former can be expressed in diopters (D) being reciprocal to the latter, which is expressed in meters.

The processing unit can further be adapted to calculate a target refraction by applying a statistical method to the statistical distribution of the measured viewing distances. The measured viewing distances can indicate the required refraction needs. The statistical method can be or include a mean, a variance, a standard deviation, a median or a maximum which allows for a surgeon to select an overall best fitting refractive correction for an artificial lens.

The distance measuring system according to the first aspect can be used before the subject's cataract surgery. The subject can wear the distance measuring system in order to gather information and extract a statistical distribution determined by the processing unit. The determined statistical distribution considers the needs of the subject and provides information for a selection and adjustment of an artificial lens type and parameters to be implanted into the subject's eye.

One exemplary implementation of the distance measuring system can be that the subject, in this case a cataract patient is provided with the device by the user, in this case a cataract surgeon or a supporting member of a medical staff, who may initialise the device for the patient. The Patient may wear the device for a required amount of time, which could be several days. Wearing of the device may be recognised by a proximity sensor and/or by a motion sensor detecting motion. The distance measuring sensor may perform continuous measurements when the patient wears a distance measuring device of the distance measuring system and may store viewing distances in the internal or external memory unit. At the next visit the patient returns the device to the user, who may download the data from the memory unit to allow processing by the processing unit. The statistical distribution may then be used to find the optimal individual refractive solution. In another exemplary implementation, the patient may perform triggered measurements under specific conditions or specific activities.

According to a second aspect of the present invention, the distance measuring system according to the first aspect can be used for selection and customisation of a refractive solution in cataract surgery. The data gathered from and determined by the distance measuring system according to the first aspect e.g. presented as statistics of refraction needs can be used to select the optimal lens or combination of lenses (refractive solution) based on the optical properties of lenses available in the database. The refractive solution can be two lenses (monofocal or multifocal) of a single type implanted in both eyes which fits the statistics of refraction needs, or two lenses with two different optical profiles which being implanted in eyes create a vision solution through binocular fusion (monovision).

With the same method customisation can be done by adjusting optical profiles of artificial lenses or manufacturing artificial lenses with required optical profiles.

According to a third aspect of the present invention, a distance measuring method is provided. The method comprises the steps of measuring viewing distances, by a distance measuring sensor of a distance measuring system, between eyes of a subject, e.g. eyes of a user, and one or more objects. The viewing distances may be measured between the eyes of the subject and the one or more objects in the distance measuring sensor's viewing direction. The method further comprises storing, by a memory unit of the distance measuring system, the measured viewing distances in a set of measured viewing distances. The method further comprises determining, by a processing unit of the distance measuring system, a statistical distribution of the measured viewing distances from the set of measured viewing distances.

The method can further comprise detecting, by an eye monitoring unit, the subject's eye direction relative to the distance measuring sensor's viewing direction. and the method may further comprise statistically weighting, selecting or discarding, by the processing unit, the measured viewing distances from the set of measured viewing distances based on the subject's eye direction relative to the distance measuring sensor's viewing direction.

The method can further comprise measuring, by a movement sensor, movements of the subject's body, for example the subject's head. The method may further comprise statistically weighting, selecting or discarding, by the processing unit, the measured viewing distances from the set of measured viewing distances based on the measured movements.

The method can further comprise measuring, by an ambient light sensor of the distance measuring system, ambient light, light intensity and/or spectral content in the distance measuring sensor's viewing direction. The method may further comprise statistically weighting, selecting or discarding, by the processing unit, the measured viewing distances from the set of measured viewing distances based on the measured ambient light, light intensity and/or spectral content.

The method can further comprise receiving, by a user interface of the distance measuring system, a user input. The method may further comprise weighting, selecting or discarding, by the processing unit, the measured viewing distances from the set of measured viewing distances based on the user input.

The method can further comprise calculating, by the processing unit, a target refraction by applying a statistical method to the statistical distribution of the measured viewing distances.

The method or parts of the method may be implemented by a computer program. The computer program may comprise program code portions for causing the steps of any one of the method aspects described herein to be performed, when the computer program is run on a computer system or on one or more computing devices, e.g. an apparatus, like the distance measuring system. The computer program may be stored on a computer-readable recording medium or may be downloadable as a signal.

The method according to the third aspect may be performed before or after cataract surgery. Alternatively, the method may be performed before, during or after contact lens or spectacle fitting.

According to a fourth aspect, a frame is provided. The frame is foldable or bendable. The frame is adapted to integrate and/or mount the distance measuring system according to the first aspect. In other words, the frame can be configured such that the distance measuring system according to the first aspect can be integrated into and/or mounted to the frame. The frame can further comprise the processing unit, the memory unit and/or the distance measuring sensor. Further, the frame is adapted to be mountable on top of glasses/spectacles. Further, the frame can comprise the user interface according to the foregoing aspects. The processing unit may be further configured to provide the measured viewing distances to the memory unit.

According to a fifth aspect, a capsule is provided. The capsule is adapted to receive the frame according to the fourth aspect. The memory unit may be further configured to provide the set of measured viewing distances to the processing unit when the capsule and the frame connect to each other/are connected to each other. Further, the memory unit may be configured to provide the set of measured viewing distances when the frame is inside the capsule and the capsule is closed. The capsule may comprise an interface adapted to connect to a computer, tablet, laptop and/or smartphone to provide the set of measured viewing distances to a network, such as a cloud. Further the capsule may comprise a storage unit to store the set of viewing distances, for example until a connection to the network is available. The capsule may comprise its own charging unit arranged and adapted to be connected to a charging device, a battery and/or a charging grid. The capsule may comprise charging leads or antenna for charging the distance measuring system and/or the frame, such that the distance measuring system is provided with power. The capsule may comprise a user interface, for example in a form of alphanumeric or graphical display or status indicators, as well as buttons for basic control of capsule functionality.

In general, the steps of any one of the method aspects described herein may equally be embodied in one or more suitable components, devices or units, e.g. in suitable components of the distance measuring system. Likewise, any of the details described with respect to the distance measuring system may be embodied as a method and/or as a computer program carrying out the method.

Figure 2:
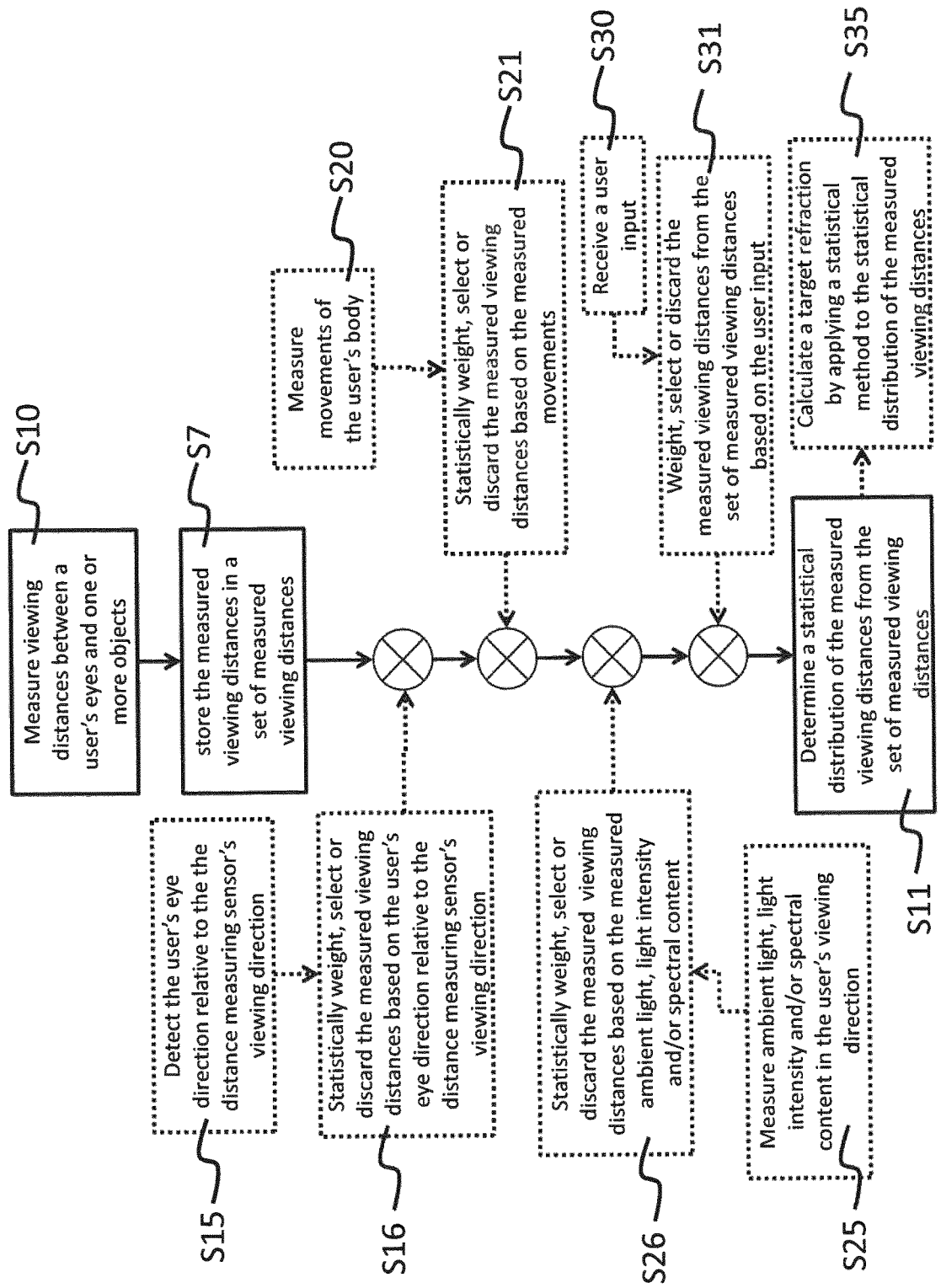
Figure 3:
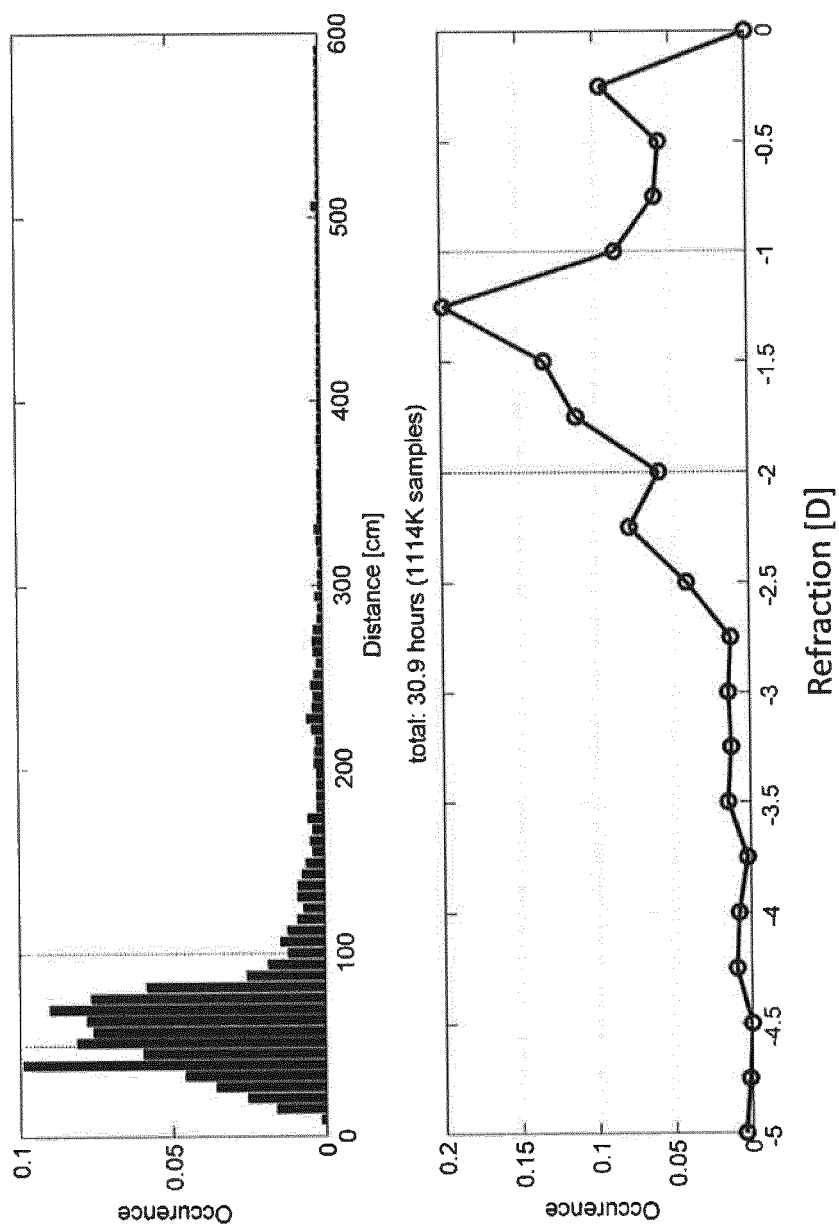
Figure 4:
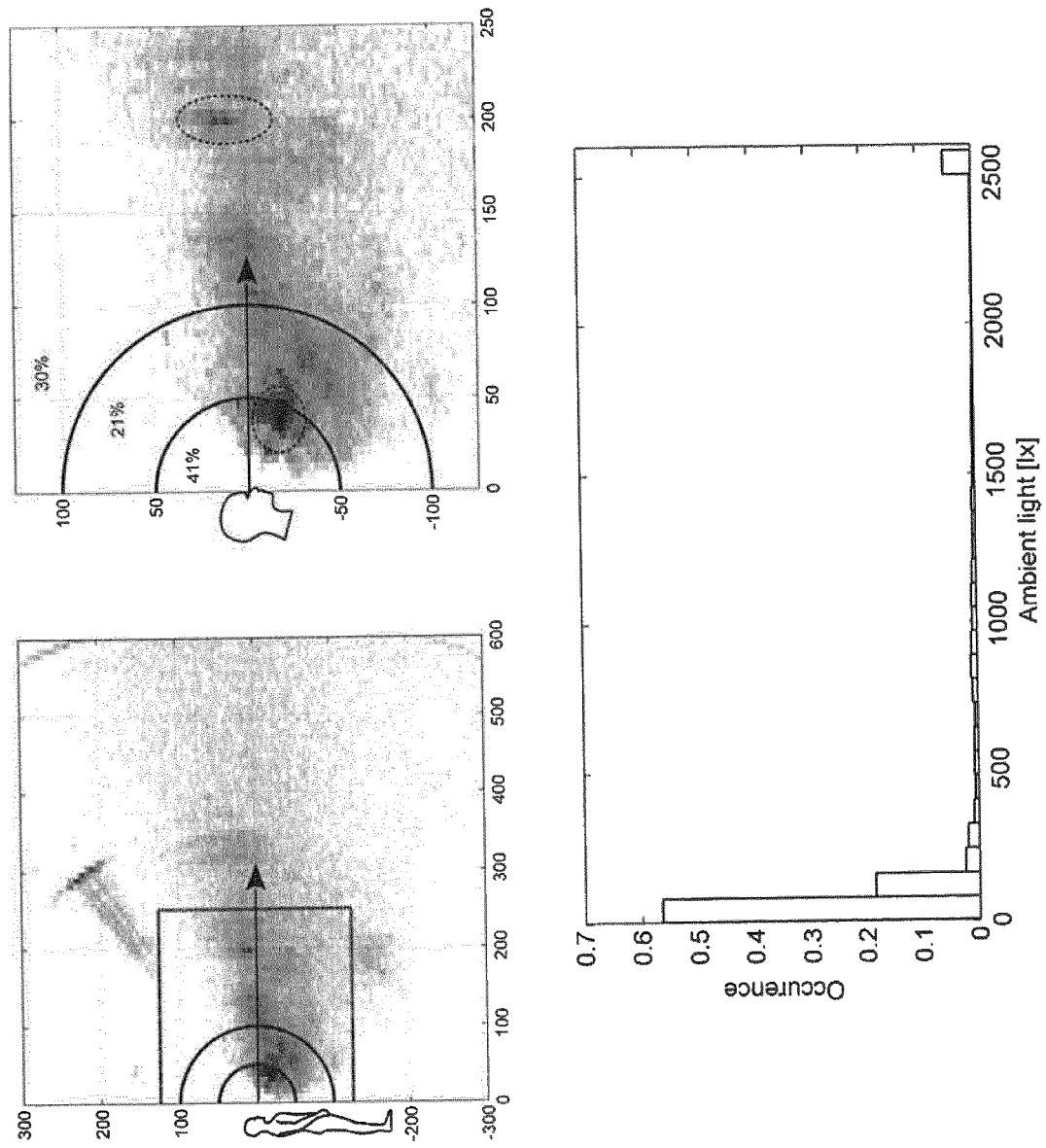
Figure 5:
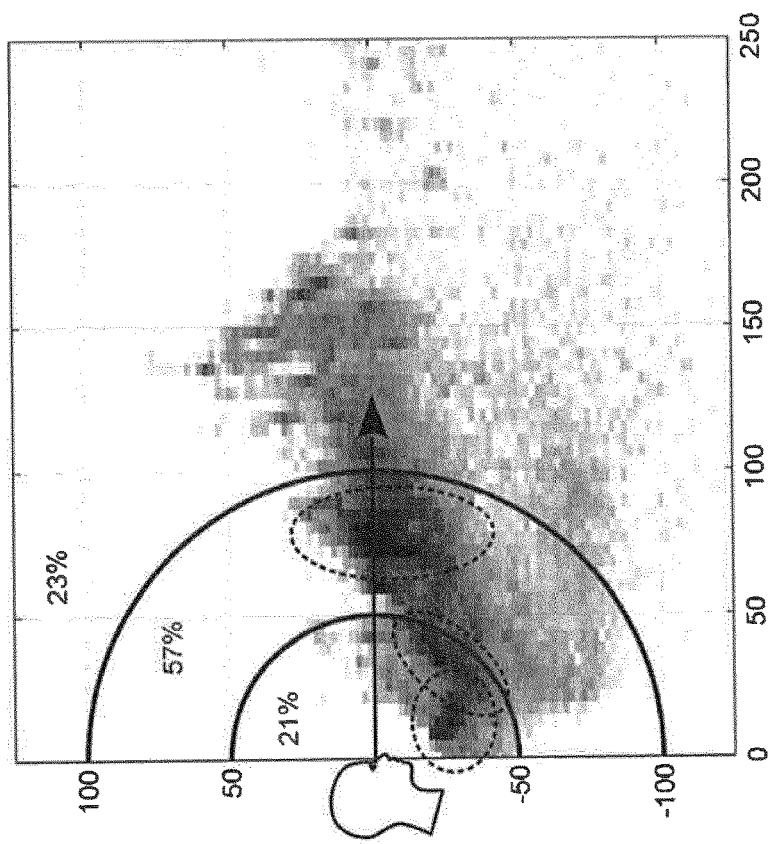
Figure 5:
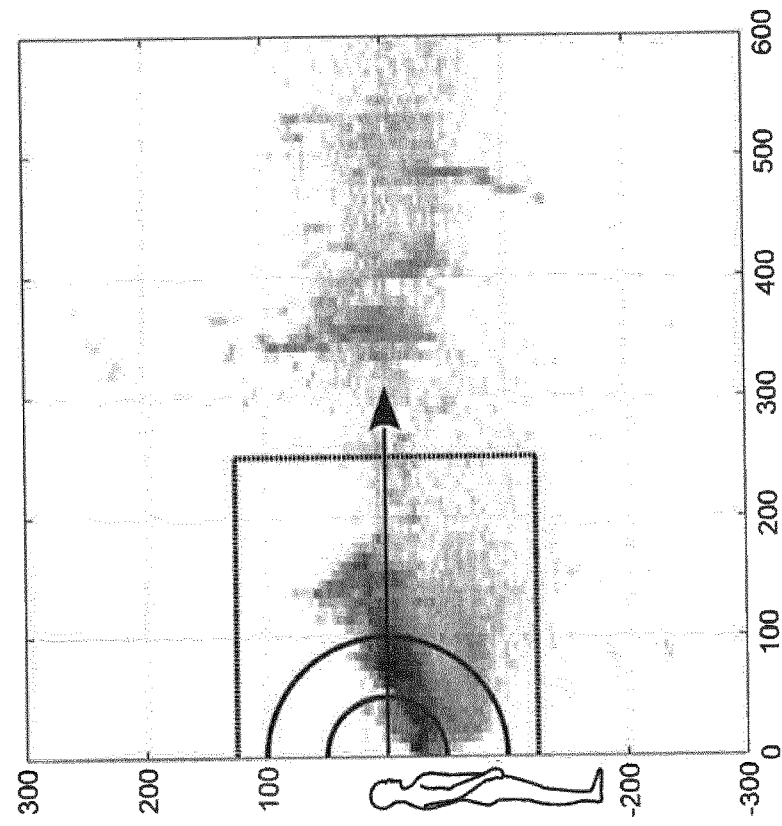
Figure 6:
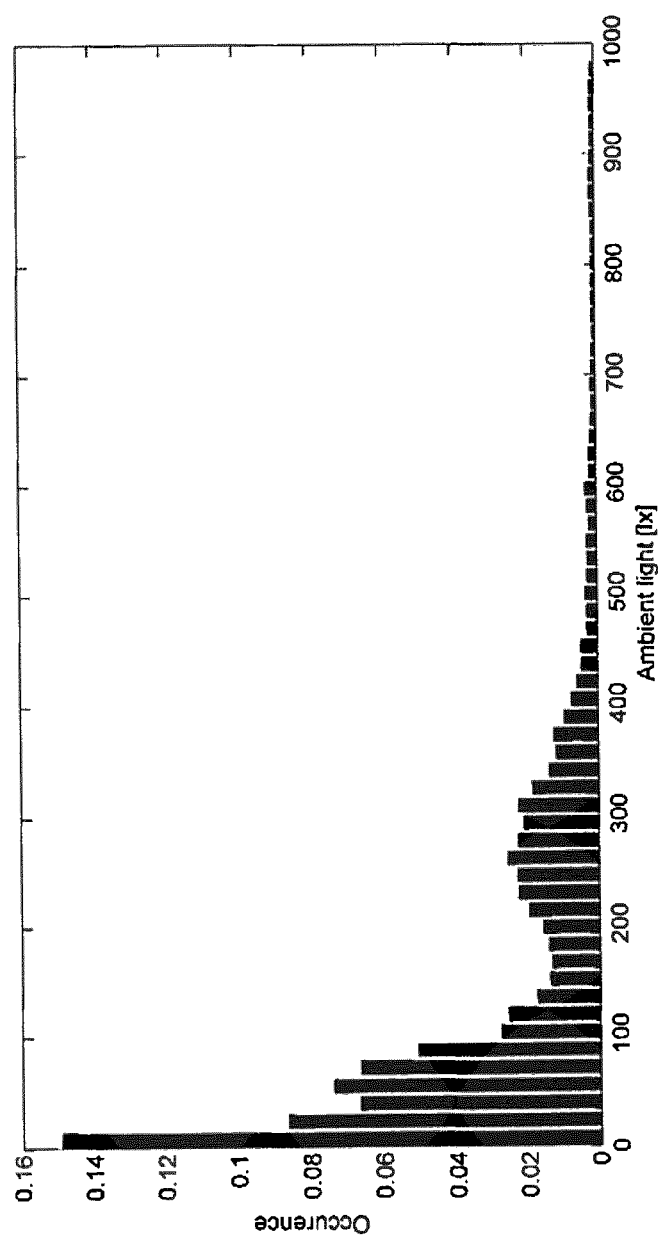
Figure 7:
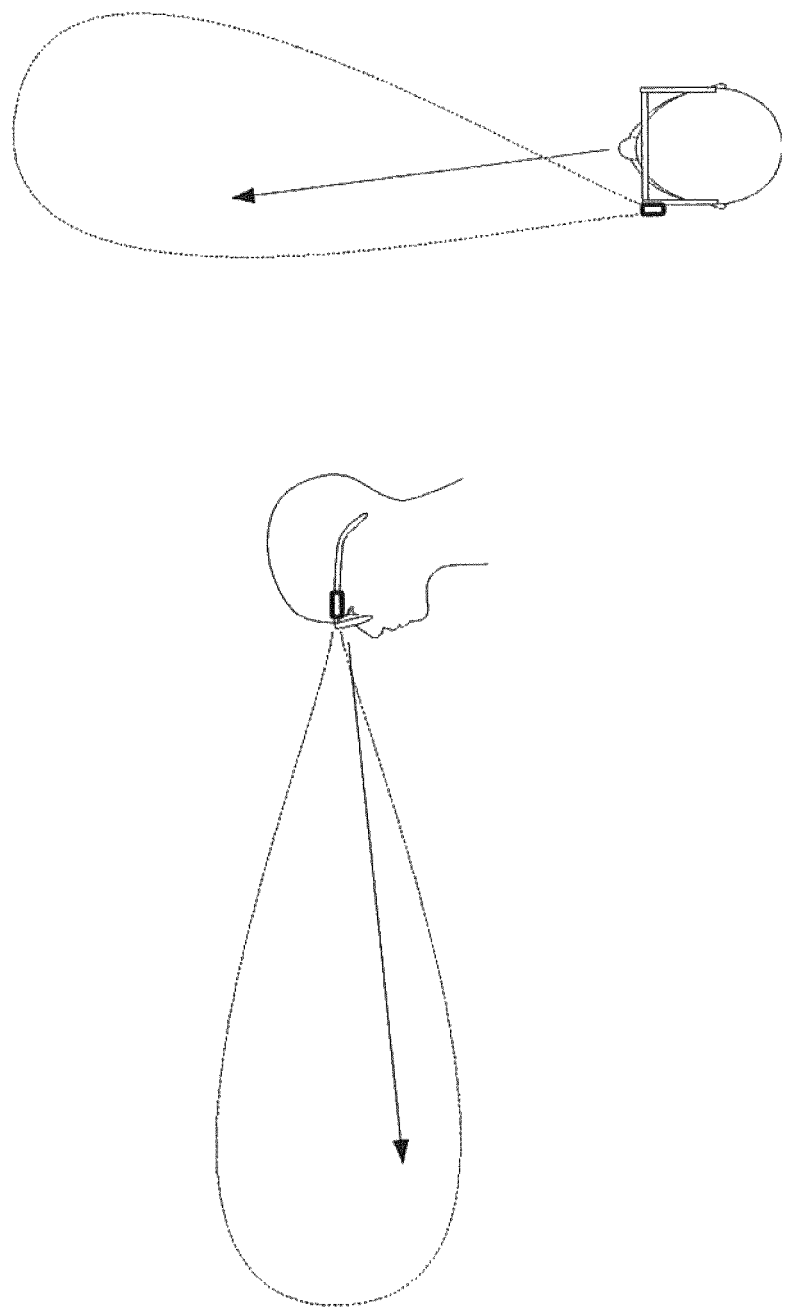
Figure 8:
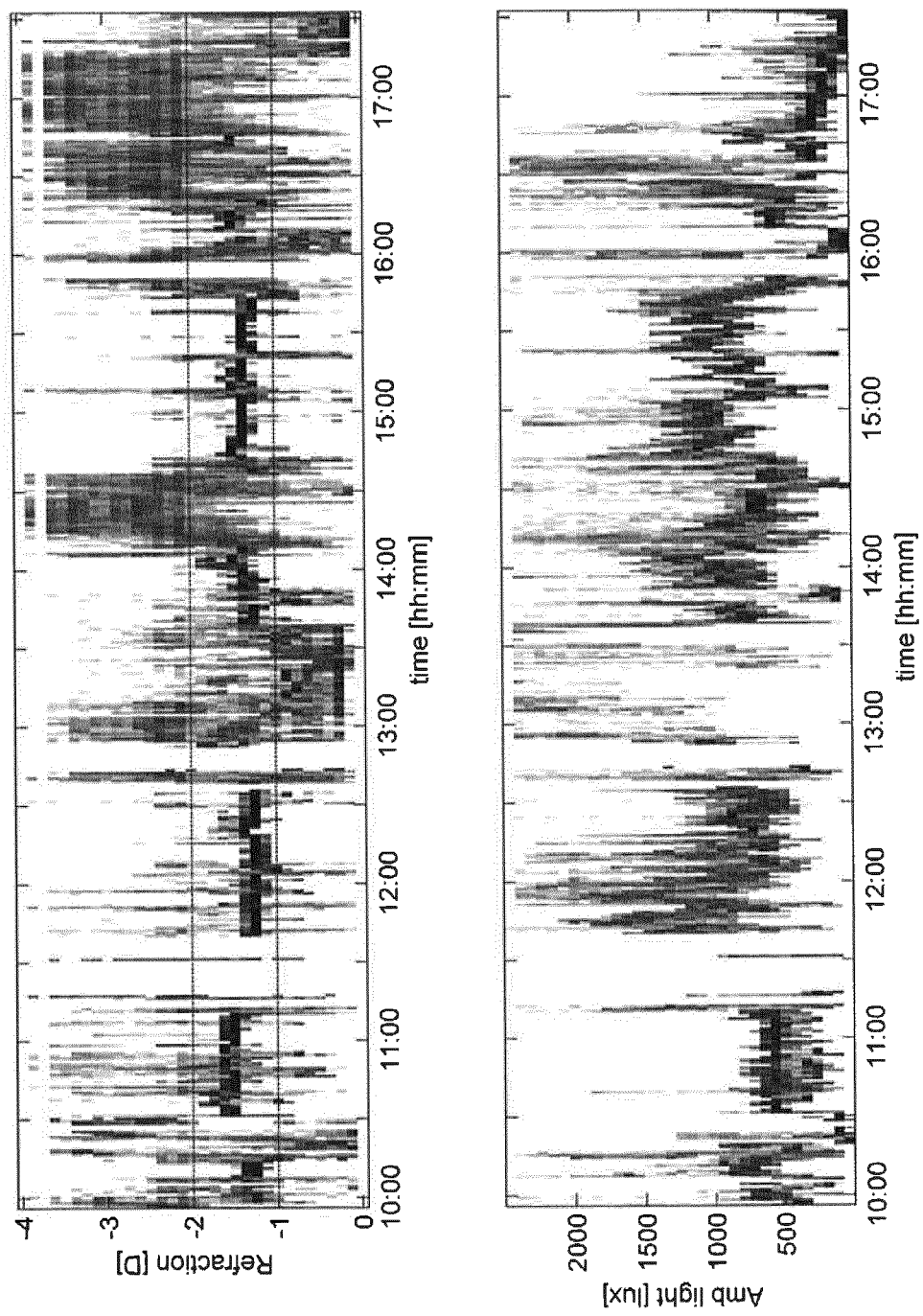
Figure 9:
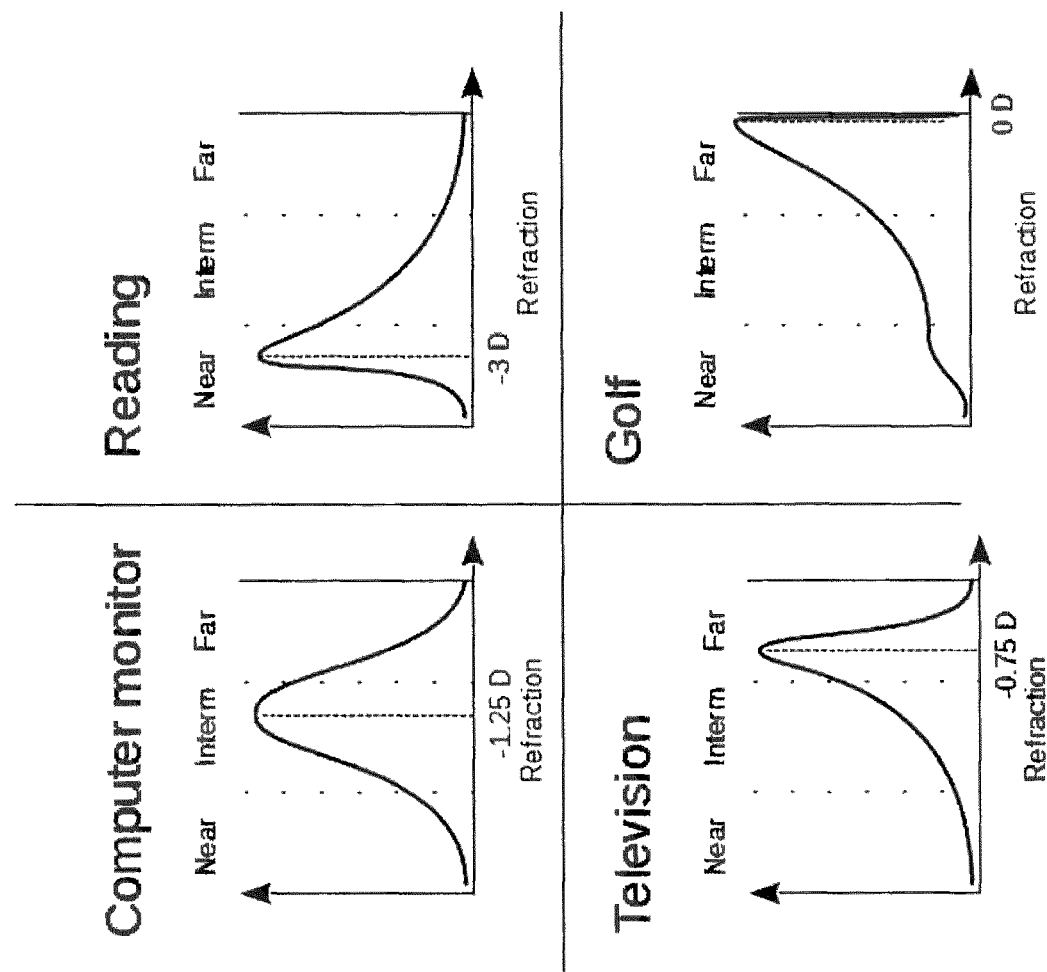
Figure 10:
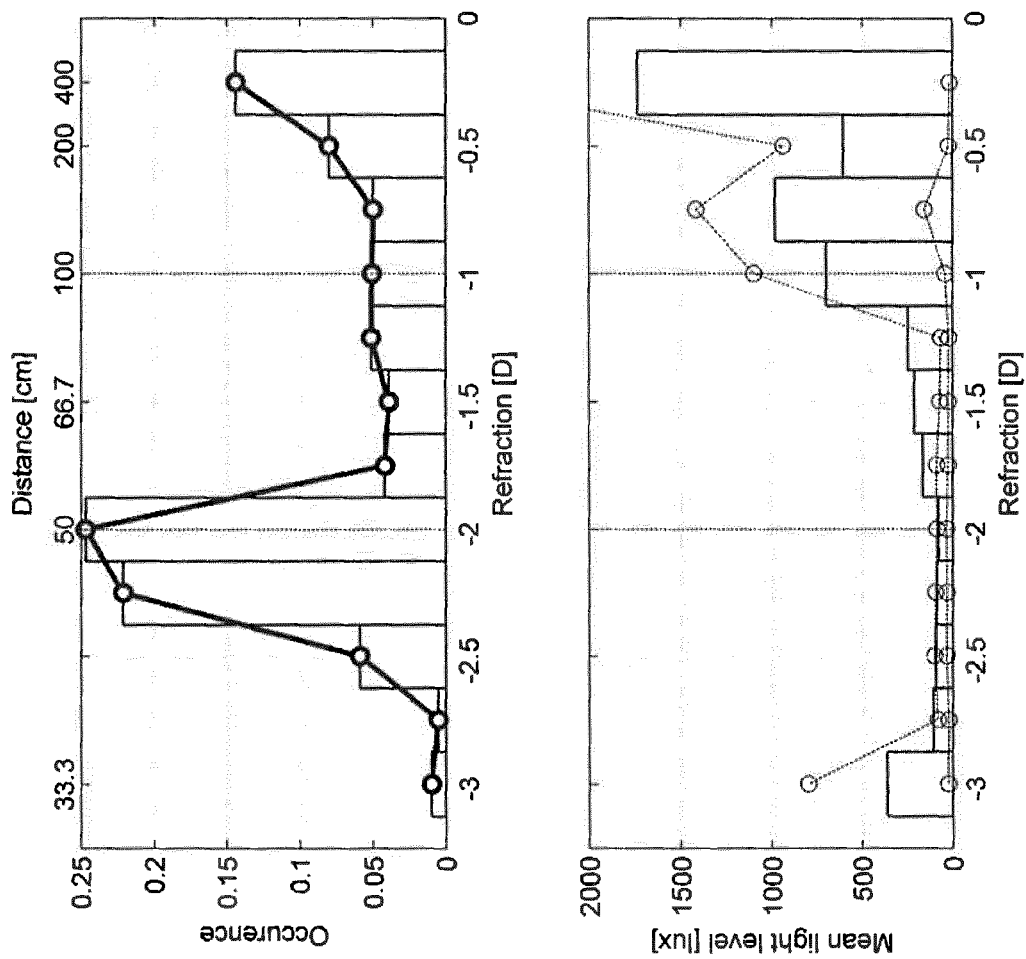
Figure 11:
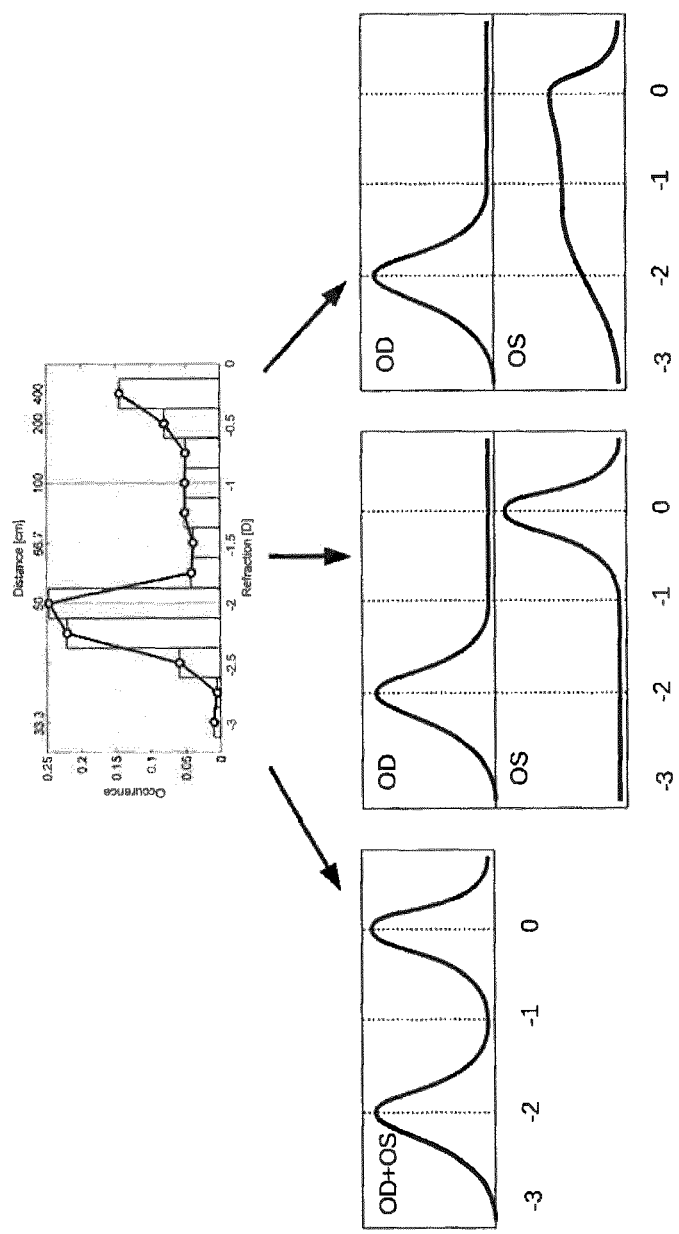
Figure 12:
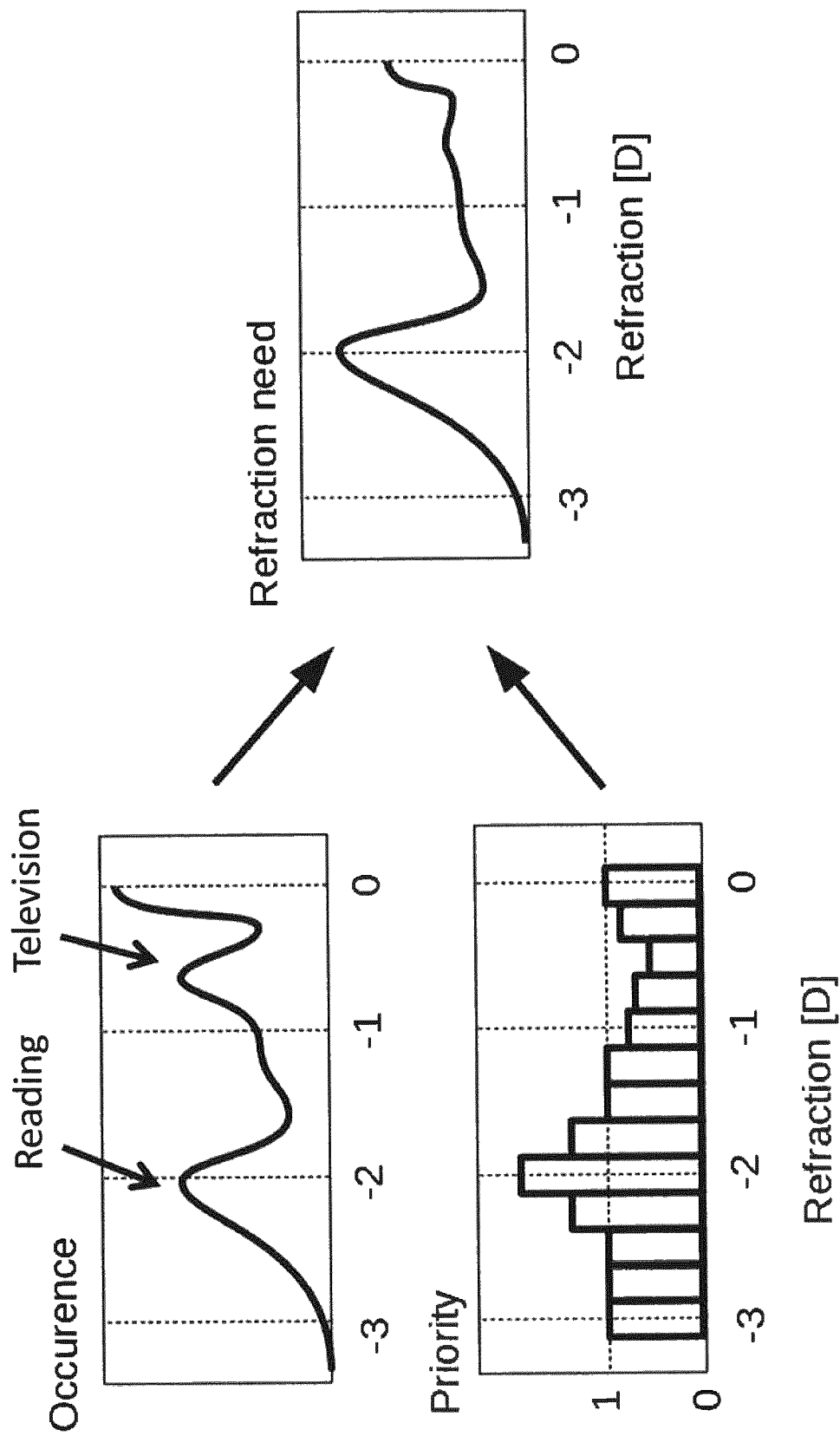
Figure 13:
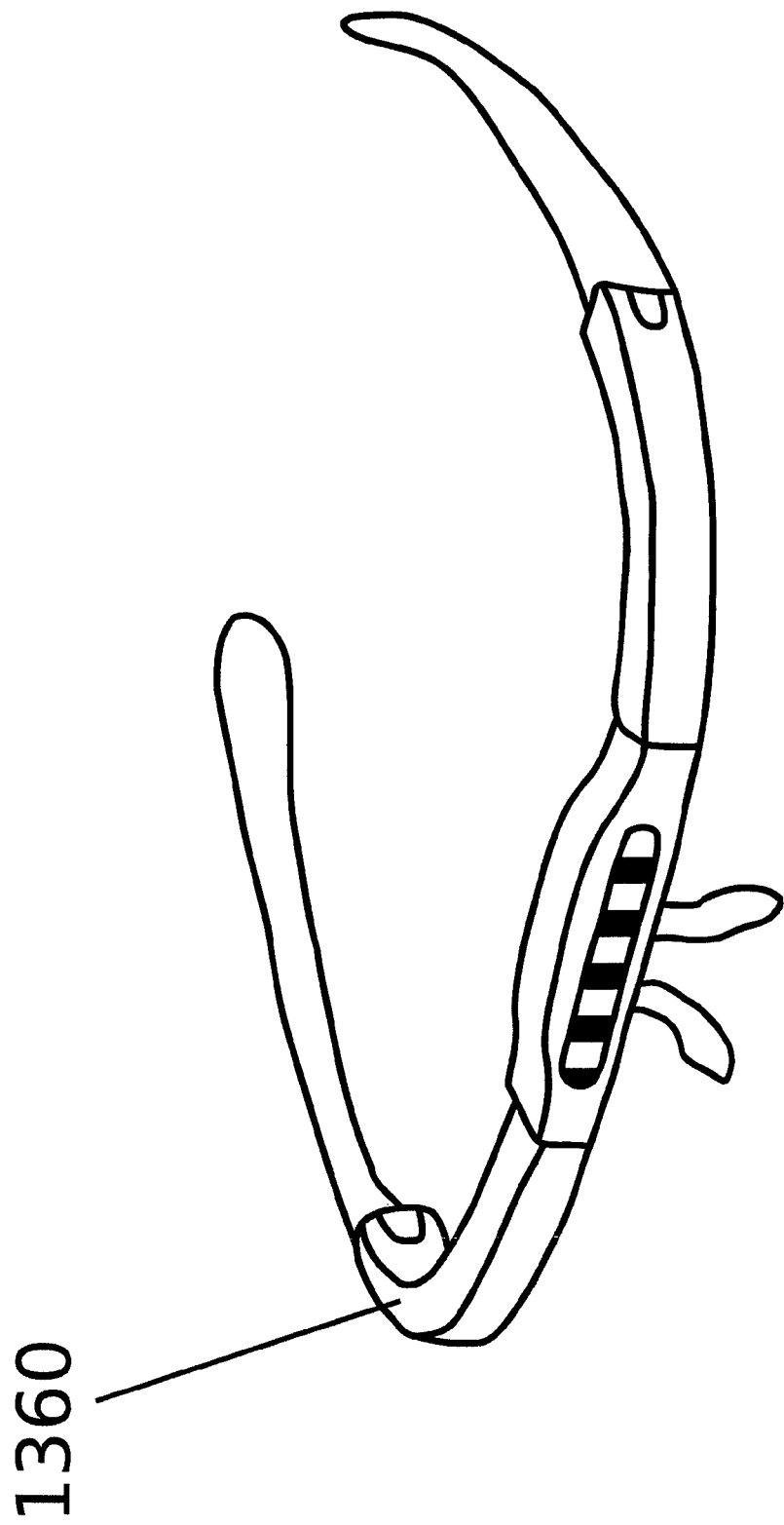
Figure 14:
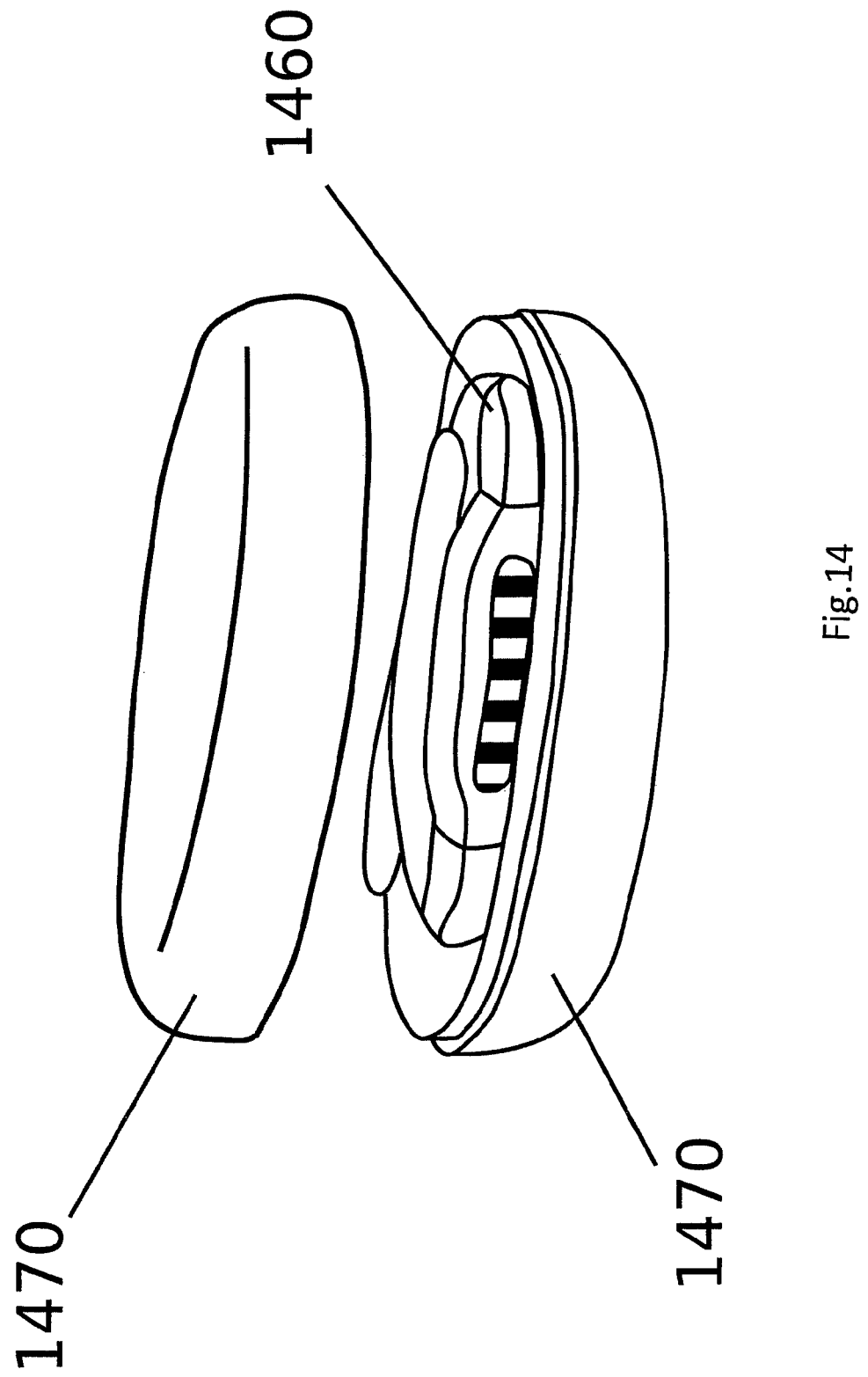

In the following, the present invention will further be described with reference to exemplary embodiments illustrated in the Figures, in which:

FIG. 1 schematically illustrates an embodiment of the distance measuring system according to the present invention;

FIG. 2 schematically illustrates an embodiment of a distance measuring method according to the present invention;

FIG. 3 schematically illustrates occurrences over distance and corresponding refraction respectively;

FIG. 4 schematically illustrates a two-dimensional distance mapping diagram and the underlying ambient light intensity distribution; dimensions on the mapping are in centimeters, half-circles indicates boundaries of the near vision zone (<50 cm), intermediate zone (between 50 and 100 cm) and far zone (above 100 cm);

FIG. 5 schematically illustrates two dimensional diagrams with respect to viewing preferences of a subject;

FIG. 6 schematically illustrates a distribution of an ambient light intensity;

FIG. 7 schematically illustrates the use of the embodiment of the distance measuring system of FIG. 1 arranged on glasses;

FIG. 8 schematically illustrates a time history of refraction requirements distribution and ambient light;

FIG. 9 schematically illustrates examples of statistical distributions of refraction requirements calculated by the embodiment of the distance measuring system for different activities;

FIG. 10 schematically illustrates distributions of refraction requirements and mean light intensities associated with specific requirements;

FIG. 11 schematically illustrates possible solutions for a realization of optimal refraction requirements distribution;

FIG. 12 schematically illustrates a prioritization mechanism of prioritized viewing distances;

FIG. 13 schematically illustrates an embodiment of the foldable or bendable frame according to the present invention; and FIG. 14 schematically illustrates an embodiment of the capsule according to the present invention.

In the following description, for purposes of explanation and not limitation, specific details are set forth, such as processing details and steps, in order to provide a thorough understanding of the present invention. It will be apparent to one skilled in the art that the present invention may be practiced in other embodiments that depart from these specific details.

Those skilled in the art will further appreciate that functions explained herein below may be implemented using individual hardware circuitry, using software functioning in conjunction with one or more processors, e.g. a programmed microprocessor or a general purpose computer, using an Application Specific Integrated Circuit (ASIC) and/or using one or more Digital Signal Processors (DSPs). It will also be appreciated that when the present disclosure is described as a method, it may also be embodied in a computer processor arrangement and a memory arrangement coupled to a processor arrangement, wherein the memory arrangement is encoded with or stores one or more programs or corresponding code to cause the processor arrangement to perform or control the methods disclosed herein when executed by the processor arrangement.

FIG. 1 schematically illustrates the distance measuring system 1 according to an embodiment of the present invention. The distance measuring system 1 comprises a distance measuring sensor 5, a memory unit 7 and a processing unit 10. Optionally, the distance measuring system 1 comprises an eye monitor unit 15, a movement sensor 20, an ambient light sensor and/or a user interface 30. The different units 5, 7, 10, 15, 20, 25 of the distance measuring system 1 can be realised in one and the same device 1 as illustrated in FIG. 1 or can be distributed in two or more separate devices to form the distance measuring system 1. Further details of the distance measuring system 1 will now be described with respect to FIG. 2.

FIG. 2 schematically illustrates a method embodiment of the present invention that can be implemented by the distance measuring system of FIG. 1. First, distance measuring sensor 5 measures one or more viewing distances in step S10. These distances are distances between a subject and one or more objects in the subject's viewing direction. Second, in step S7, the memory unit 7 stores the measured viewing distances in a set of measured viewing distances. Third, in step S11, the processing unit 10 determines a statistical distribution of the measured viewing distances from the set of measured viewing distances.

In the following, some optional steps shown in FIG. 2 will be described. These optional steps usually lead to an improved, e.g. more precise, evaluation. For example, eye monitoring unit 15 detects, in optional step S15, the subject's eye direction relative to the distance measuring sensor's direction, e.g. viewing direction. In optional step S16, the processing unit 10 statistically weights, selects or discards the measured viewing distances from the set of measured viewing distances based on the subject's eye direction relative to the distance measuring sensor's direction, e.g. viewing direction. Instead of discarding the measured viewing distances, the processing unit 10 may select specific viewing distances regarded valuable or select subject preferred viewing distances or weight the measured viewing distances with a weighting factor smaller or higher than one. In optional step S20, a movement sensor 20 measures S20 movements of the subject's body. In the present example, the movement sensor 20 comprises an accelerometer and a gyroscope, but may further comprise different sensors like for example a magnetometer, an altimeter, a pedometer or a geopositioning device. In optional step S21, the processing unit 10 statistically weights, selects or discards the measured viewing distances from the set of measured viewing distances based on the measured movements. If a subject's head is at least substantially steadily pointed to a measured object, the object is measured in distance and weighted by a factor of one or higher than one. If the subject's attention is distracted, e.g. when a subject's head is moving at least substantially constantly around an object, the measured distance is weighted by a factor smaller than 1 or discarded and therefore not considered in the overall statistical distribution.

Ambient light sensor 25, which may also be extended by using an additional colour sensor, measures ambient light and/or light intensity and/or spectral content in the subject's viewing direction in optional step S25. The processing unit 10 statistically weights, selects or discards the measured viewing distances from the set of measured viewing distances based on the measured ambient light, light intensity and/or spectral content in optional step S26. The ambient light affects the subject's eye accommodation and depth-of-focus. Under bright illumination, when the pupil of the subject is constricted and subject's depth-of-focus is significantly increased, the measured viewing distances are deprioritized and weighted by values lower one. When considering dim light, for example when the subject is reading a book and the subject's pupils are dilated, which corresponds to ambient light associated with dim illumination, the measured viewing distances are prioritized and weighted by values higher than one.

In optional step S30, a user interface 30 receives a user input. In optional step S31, the processing unit 10 weights, selects or discards the measured viewing distances from the set of measured viewing distances based on the user input. The subject may use a tap on the distance measuring system 1, on attached devices or on glasses which comprise the distance measuring system 1, in order to weight, select or discard the measured viewing distances. The subject's input can further be head gestures like nodding or shaking, detected by head motion sensor, subject or eye movement, detected by the eye monitoring device. For example, a subject might discard measured viewing distances by looking aside from the object to be measured, directly leading to discarded measuring results, because of the so adjusted eye monitoring device. Another example might be a subject putting his or her hands in front of the sensor with a waving hand gesture or keeping his or her hand in front of the distance measuring system 1 for a few seconds to discard or weight measured viewing distances.

One or more, e.g. all of the aforementioned weighting or discarding steps may be performed independently from each other or together in a common processing step.

Finally, the processing unit 10 calculates, in optional step S35, a target refraction by applying a statistical method to the statistical distribution of the measured viewing distances from the set of measured viewing distances. The target refraction, respectively the refractive corrections for an artificial lens, is derived from refractive target diagrams described as refractive requirements diagram in FIG. 8 below. Theses diagrams directly correlate with the distance occurrence measurement results from a distance occurrence diagram exemplarily described in FIG. 3 below.

FIG. 3 shows a distance occurrence diagram over distance in centimetres (cm). The diagram of FIG. 3 serves an example for distance occurrences that can be obtained by the distance measuring system 1 of FIG. 1 with the method steps of FIG. 2. The occurrence diagram shows the probability of distance occurrences over specific distances based on actual measurements. By converting distance to refraction the refraction statistics can be obtained. By analysing the refraction statistics (distribution) in FIG. 3, the surgeon is able to derive the target refraction or required depth-of-focus from the refractive requirements diagram for one or both eyes. In consequence the surgeon can obtain a statistically best fitting IOL as e.g. characterised by a specific thought-focus-curve (visual acuity or optical quality as a function of viewing distance or refractive addition) for a patient, who used or was wearing the distance measuring system 1 for a certain amount of time. The certain amount of time can be several hours or even several days and is shown to be 30.9 hours in the illustrated scenario of FIG. 3. The 30.9 hours lead to 1114K samples of distances for a patient. This duration may be considered as an example mean time for use of/wearing of such a device by a patient.

FIG. 4 illustrates two dimensional maps of viewing range distributions of a person wearing the distance measuring system 1 of FIG. 1. The two dimensional maps comprise a vertical viewing distance and horizontal viewing distance. The diagrams indicate horizontal distances from 0 to 600 cm in horizontal direction and 0 to 300 cm in vertical direction. Underlying measurements are shown in the lower plot, which illustrates occurrences of specific ambient light intensities. Darker colors in the upper plot indicate a higher occurrence rate. It is shown a subject body and head being scaled to the dimensions of the two upper plots. Highlighted zones (dashed ovals) in the plots are shown starting from the left: a laptop area and a television screen. The zoomed-in diagram on the right-hand-side illustrates further results of the patient and his preferred activities during an office day. As can be seen therefrom, the most occurrences happened within a short range of viewing distances and thus in near vision, for example when the patient was using his laptop or the like. In the specific example of FIG. 4, 41% of the occurrences happened in near vision. Less occurrences happened in an intermediate range (intermediate vision), for example when the patient had conversations with others, and the least occurrences happened in a far range (far vision), for example when the patient was looking out of a window in front.

The occurrence diagram down below schematically illustrates occurrences of specific ambient light during the activities of using a laptop and watching TV. The distance map and the occurrences diagram build the foundation for the illustrated results shown in FIGS. 11 and 12.

FIG. 5 schematically illustrates another two dimensional distance distribution when the patient was wearing the distance measuring system 1 of FIG. 1 at home. The left diagram illustrates distances in horizontal direction from 0 to 600 cm and 0 to 300 cm in vertical direction. The right diagram illustrates a zoomed-in diagram with preferred activities of the patient shown with dashed ovals. From left to right areas correspond to desktop work, reading and computer screen, respectively. The probability of tasks performed often is highlighted in a darker black colour, wherein light colour indicates tasks performed less often.

FIG. 6 schematically illustrates distance occurrences over ambient light obtained by the distance measuring system 1 with the optional ambient light sensor 25 according to FIG. 1. Information about the ambient light can be considered to weight distance occurrences. Illumination conditions, e.g. the ambient light and/or light intensities occurring during different activities, in different times of day can influence the size of the pupil and thus modify the vision requirements. Moreover, the information about the ambient light can be used for weighting or discarding measured viewing distances to get a more profound analysis of the statistical distribution of measured viewing distances. The subject's activities reflect daily exposures to different ambient lights in association with the measured viewing distances. This additional measurement provides a more robust objective solution to a patient's daily accommodation needs. For example, two patients may need the same distance accommodation, but are exposed by different ambient light throughout a daily routine, which will lead to different overall refractive requirements for both patients.

FIG. 7 schematically illustrates a scenario of a patient wearing glasses to which the distance measuring system 1 of FIG. 1 is attached or which comprise the distance measuring system 1 of FIG. 1. The distance measuring system 1 may be implemented as a distance measuring device having a range distance sensor in FIG. 7. The patient looks in a gaze direction, wherein the sensor is sensitive to this gaze direction. This is illustrated in a top view and a side view illustrating the sensor sensitivity in a direction of the sensing area corresponding to the patient's viewing direction. The distance measuring device having the distance measuring sensor moves with the movement of the patient's head. Thus, every distance in the line of the patient's head direction can be sampled. Additional sensors comprised in the distance measuring system 1 help to concentrate the gathered information about the measured viewing distances to only the most important distances, which are to be considered in the final statistical distribution. The final statistical distribution indicates the measured viewing distances which occurred most often and neglects measured viewing distances which were found to be negligible. Therefore, a surgeon is able to make a profound choice of a refractive correction applied to an artificial lens together with the patient.

FIG. 8 schematically shows an illustration of the time history of a refraction requirements distribution (upper plot) and ambient light distribution (lower plot) in accordance with the acquired data of FIG. 3, which was acquired over time, whereby FIG. 8 illustrates data over a time axis. Darker colors indicate a higher occurrence rate. Typical office time is shown. Periods of the desktop monitor with refraction between −2 and −1 diopters are shown. Lunch time between 12:45 and 13:30 shows broader distribution of larger distances (smaller refraction). Desktop work (16:20 till 17:15) is observed as period with shorter distances (larger refraction).

FIG. 9 illustrates four different exemplary refractive requirements diagrams derived by way of the distance measuring system 1 of FIG. 1. The different exemplary refractive requirements diagrams are assigned to specific contexts. For example, when a patient uses a PC, the refraction requirement is lower in magnitude than the refraction requirement for reading, but higher than the refraction requirement for watching TV or playing golf. The refraction requirements of the specific activities can then be integrated into a combined diagram based on the patient's individual preferences, wishes and/or time spent in specific activities. In this way the patient is able to prioritise or deprioritise certain activities and with this feature he is able to adjust a weight of contribution to the overall statistics. For example, the patient might prefer to elevate activities, where dependence on glasses would be a higher burden, for example, when it is accompanied by a physical activity. In contrast, the patient might be willing to depreciate activities, where vision quality is not critical, even when he or she is spending significant amount of time in this activity. The refractive target can be individualised in such manner according to an interview between the patient and the doctor before the surgery and then be used for the selection of an IOL type and specific parameters. Such individual tuning is not possible when the overall statistics are estimated purely on the time basis and thus without stratification of data based on the activities.

FIG. 10 schematically illustrates refraction requirements and mean light intensities associated with refraction, calculated from the distance measurements illustrated on FIG. 4. The peak at refraction −2D corresponds to usage of a laptop computer, which might be considered the most preferred distance of this specific subject. Further considerations for manufacturing an artificial lens may be extracted by using the following diagrams of FIG. 11.

FIG. 11 schematically illustrates possible solutions for a realization of optimal refraction requirements extracted from FIGS. 4 and 10 respectively. This realisation of optimal refraction requirements curves are based on the through-focus curves (TFC) of intraocular lenses, which are shown from Left-to-right. The first diagram on the left below illustrates a diagram for a multifocal IOL, whereby both eyes (OD and OS) are getting an implant which considers both maximum refractive corrections of −2D and OD. The second diagram in the middle below illustrates a diagram for two monofocal lenses, wherein one eye (OD) is getting an implant of a monofocal lens matching the −2D target, while the other (OS) is getting an implant of a monofocal lens matching the OD target. The OD target corresponds to a plano lens with 0 diopters to match distance vision, the so called monovision. The third diagram on the right below illustrates a diagram for two monofocal lenses, wherein one eye (OD) is getting an implant of a monofocal lens as in the second diagram, while the other eye (OS) is getting an implant of a lens with an extended depth of field between −2 and 0 diopters. The statistical distribution determined herein enables a medical professional to determine a well-suited monofocal IOL or an even better suited multifocal IOL.

FIG. 12 schematically illustrates a prioritization mechanism of prioritized viewing distances. An occurrence diagram, a priority diagram and a refraction need diagram are shown. The refraction need diagram is derived from the combination of the priority diagram and the refraction need diagram. In the occurrence diagram the peak around −2D (reading) is elevated based on a prioritization feedback shown in the refraction need diagram below the occurrence diagram, while a peak around −0.7D (TV), which was deprioritized based on the patient feedback, is reduced in the final refraction need diagram. Therefore, a better solution for an artificial lens can be found by introduction of a specific prioritization, wherein the circumstances for prioritization can be different for each individual.

The distance measuring method and the distance measuring system as illustrated in the figures above can be further enhanced by the embodiments illustrated in FIGS. 13 and 14.

FIG. 13 schematically illustrates an embodiment of the foldable or bendable frame 1360 according to the present invention. The frame 1360 is provided with the distance measuring unit as described with respect to FIGS. 1 and 2, the corresponding sensors, the processing unit, the memory unit and a separate battery. The frame 1360 can be worn separately or on top of prescription glasses. The frame 1360 can be formed in a shape of normal glasses without having glasses itself. Further, the frame 1360 is provided with basic user input possibilities, like single buttons. The foldable frame 1360 can also report a functioning status, such as ok/error. Since the frame 1360 comprises the distance measuring system, the sets of measured viewing distances can be collected in the corresponding memory unit. To further provide enhancement to the specific subject in use, the frame 1360 can be delivered together with a capsule as shown in FIG. 14.

FIG. 14 schematically illustrates an embodiment of the capsule 1470 according to the present invention. The capsule is able to receive the frame 1460. The capsule is used for protection reasons, downloading data, charging of the frame 1460, connecting the capsule 1470 to tablet/laptop/smartphone per wire or wirelessly. Thus, the frame 1460 can be made lighter, since it does not need a transmitting unit on its own. The capsule 1470 can store data according to multiple session by its own memory unit. Further, the capsule 1470 can also have a display for displaying further information, for example error messages/reports. The capsule 1470 can further be adapted to upload data on the cloud via a wireless connection, such as Bluetooth or wireless local area networking. The capsule 1470 can further be adapted to store data on external non-volatile data storage media, such as memory card or drive. In the case of the subject travelling, the capsule 1470 is provided with a battery case for a battery to be inserted, as well as contact leads to be used for charging via a charging grid.

The combination of the frame and the capsule as illustrated in FIGS. 13 and 14 provide a simple possibility for a subject to carry around the distance measuring system as illustrated in FIG. 1. The subject can then make use of the distance measuring system as illustrated in FIG. 7 on the go and on own preferences.

By way of the technique described herein, customised ablation profiles can be determined. Current refractive lasers are considering current refractive power (and/or the corneal radius of curvature—corneal power and/or total wavefront aberrations of the eye) and target refractive power and estimate the ablation profile based on the difference. The technique described herein enables to calculate a customised ablation profile in order to realise the desired vision performance of the eye. For example, this could be an extended depth of field. Thus, the measurements described herein can serve as an input to the calculation of ablation profiles to realise required optical power and depth of field.

The invention claimed is:

1. A distance measuring system comprising:
    a distance measuring sensor adapted and arranged to measure viewing distances between eyes of a subject and one or more objects; and
    a memory unit adapted to store the measured viewing distances in a set of measured viewing distances;
    a processing unit adapted to determine a statistical distribution of the measured viewing distances from the set of measured viewing distances.

2. The distance measuring system according to claim 1, further comprising:
    an eye monitoring unit adapted and arranged to detect the subject's eye direction relative to the distance measuring sensor's viewing direction, wherein the processing unit is further adapted to statistically weight, select or discard the measured viewing distances from the set of measured viewing distances based on the subject's eye direction relative to the distance measuring sensor's viewing direction.

3. The distance measuring system according to claim 1, further comprising:
a movement sensor, for example an accelerometer and a gyroscope, wherein the movement sensor is adapted and arranged to measure movements of the subject's body, for example the subject's head, wherein the processing unit is further adapted to statistically weight, select or discard the measured viewing distances from the set of measured viewing distances based on the measured movements.

4. The distance measuring system according to claim 1, further comprising:
an ambient light sensor adapted and arranged to measure ambient light, light intensity and/or spectral content in the distance measuring sensor's viewing direction, wherein the processing unit is further adapted to statistically weight, select or discard the measured viewing distances from the set of measured viewing distances based on the measured ambient light, light intensity and/or spectral content.

5. The distance measuring system according to claim 1, further comprising:
a user interface adapted to receive a user input, wherein the processing unit is further adapted to weight, select or discard the measured viewing distances from the set of measured viewing distances based on the user input.

6. The distance measuring system according to claim 1, wherein the distance measuring system is adapted to be mounted on glasses, spectacles' frame and/or adapted to be attached to the subject's head.

7. The distance measuring system according to claim 1, wherein the processing unit is further adapted to calculate a target refraction by applying a statistical method to the statistical distribution of the measured viewing distances.

8. The distance measuring system according to claim 1, employed for selection and customisation of a refractive solution in cataract surgery.

9. A frame adapted to integrate and/or mount the distance measuring system according to claim 1, wherein the frame is foldable or bendable.

10. The frame according to claim 9, wherein the frame is adapted to be received by a capsule.

11. A distance measuring method comprising the steps of:
measuring viewing distances, by a distance measuring sensor of a distance measuring system, between eyes of a subject and one or more objects;
storing, by a memory unit, the measured viewing distances in a set of measured viewing distances; and
determining, by a processing unit of the distance measuring system, a statistical distribution of the measured viewing distances from the set of measured viewing distances.

12. The method according to claim 11, further comprising:
detecting, by an eye monitoring unit of the distance measuring system, the subject's eye viewing direction relative to the distance measuring sensor's viewing direction; and
statistically weighting, selecting or discarding, by the processing unit, the measured viewing distances from the set of measured viewing distances based on the subject's eye direction relative to the distance measuring sensor's viewing direction.

13. The method according to claim 11, further comprising:
measuring, by a movement sensor of the distance measuring system, movements of the subject's body, for example the subject's head; and
statistically weighting, selecting or discarding, by the processing unit, the measured viewing distances from the set of measured viewing distances based on the measured movements.

14. The method according to claim 11, further comprising:
measuring, by an ambient light sensor, ambient light, light intensity and/or spectral content in the distance measuring sensor's viewing direction; and
statistically weighting, selecting or discarding, by the processing unit, the measured viewing distances from the set of measured viewing distances based on the measured ambient light, light intensity and/or spectral content.

15. The method according to claim 11, further comprising:
receiving, by a user interface of the distance measuring system, a user input; and
weighting, selecting or discarding, by the processing unit, the measured viewing distances from the set of measured viewing distances based on the user input.

16. The method according to claim 11, further comprising:
calculating, by the processing unit, a target refraction by applying a statistical method to the statistical distribution of the measured viewing distances.

17. The method according to claim 11, wherein the method is performed before or after cataract or refractive surgery, or before, during or after contact lens or spectacle fitting.

* * * * *